US008170320B2

(12) United States Patent
Smith et al.

(10) Patent No.: US 8,170,320 B2
(45) Date of Patent: May 1, 2012

(54) MAMMOGRAPHY/TOMOSYNTHESIS SYSTEMS AND METHODS AUTOMATICALLY DERIVING BREAST CHARACTERISTICS FROM BREAST X-RAY IMAGES AND AUTOMATICALLY ADJUSTING IMAGE PROCESSING PARAMETERS ACCORDINGLY

(75) Inventors: Andrew Paul Smith, Lexington, MA (US); Biao Chen, Newark, DE (US); Zhenxue Jing, Southbury, CT (US)

(73) Assignee: Hologic, Inc., Bedford, MA (US)

( * ) Notice: Subject to any disclaimer, the term of this patent is extended or adjusted under 35 U.S.C. 154(b) by 563 days.

(21) Appl. No.: 12/396,978

(22) Filed: Mar. 3, 2009

(65) Prior Publication Data
US 2010/0226475 A1    Sep. 9, 2010

(51) Int. Cl.
*G06K 9/00*    (2006.01)
(52) U.S. Cl. ...................................................... 382/132
(58) Field of Classification Search ................. 396/132; 382/132
See application file for complete search history.

(56) References Cited

U.S. PATENT DOCUMENTS

| | | | |
|---|---|---|---|
| 4,496,557 A | | 1/1985 | Malen et al. |
| 4,907,156 A | * | 3/1990 | Doi et al. ...................... 382/130 |
| 5,051,904 A | | 9/1991 | Griffith |
| 5,359,637 A | | 10/1994 | Webber |
| 5,657,362 A | * | 8/1997 | Giger et al. ..................... 378/37 |
| 5,825,936 A | * | 10/1998 | Clarke et al. .................. 382/261 |
| 6,278,793 B1 | * | 8/2001 | Gur et al. ....................... 382/128 |
| 6,289,235 B1 | | 9/2001 | Webber et al. |
| 6,647,092 B2 | | 11/2003 | Eberhard et al. |
| 6,885,724 B2 | | 4/2005 | Li et al. |
| 7,123,684 B2 | | 10/2006 | Jing et al. |
| 7,142,633 B2 | * | 11/2006 | Eberhard et al. ................. 378/62 |
| 7,245,694 B2 | | 7/2007 | Jing et al. |
| 7,764,820 B2 | * | 7/2010 | Wu et al. ........................ 382/132 |
| 7,881,513 B2 | * | 2/2011 | Bernard et al. ................ 382/128 |
| 2001/0038681 A1 | | 11/2001 | Stanton et al. |
| 2004/0066884 A1 | | 4/2004 | Hermann Claus et al. |
| 2004/0101095 A1 | | 5/2004 | Jing et al. |
| 2004/0109529 A1 | | 6/2004 | Eberhard et al. |
| 2005/0027188 A1 | | 2/2005 | Metaxas et al. |
| 2005/0105679 A1 | | 5/2005 | Wu et al. |
| 2005/0129172 A1 | | 6/2005 | Mertelmeier |
| 2006/0110022 A1 | * | 5/2006 | Zhang et al. ................... 382/132 |
| 2007/0274585 A1 | | 11/2007 | Zhang et al. |
| 2008/0033657 A1 | | 2/2008 | Cline et al. |
| 2008/0037853 A1 | * | 2/2008 | Bernard et al. ................ 382/132 |
| 2008/0205717 A1 | | 8/2008 | Reeves et al. |

(Continued)

FOREIGN PATENT DOCUMENTS

WO    WO03/020114 A2    3/2003

(Continued)

OTHER PUBLICATIONS

"Lorad Selenia" Document, B-BI-SEL US/Intl(May 2006) © Hologic 2006.

(Continued)

*Primary Examiner* — Rodney Fuller
(74) *Attorney, Agent, or Firm* — Cooper & Dunham, LLP

(57) ABSTRACT

Methods and systems that automatically identify breast characteristics such as x-ray density and breast texture from initial x-ray images of the breast and automatically adjust process parameter setting of image processing algorithms that operate on the initial images to derive processing images suitable for display or further processing.

20 Claims, 8 Drawing Sheets

U.S. PATENT DOCUMENTS

2009/0004205 A1  1/2009 Clarke et al.
2009/0220138 A1* 9/2009 Zhang et al. ................ 382/132

FOREIGN PATENT DOCUMENTS

WO  WO2006/058160 A2  6/2006

OTHER PUBLICATIONS

"Digital Clinical Reports: Tomosynthesis", GE Brochure, 98-5493 11/98, 1998.

"Essentials for life: Senographe Essential Full-Field Digital Mammography system", GE Health-care Brochure, MM-0132-05.06-EN-US, 2006.

Cole, Elodia, et al., "The Effects of Gray Scale Image Processing on Digital Mammography Interpretation Performance", *Academic Radiology*, vol. 12, No. 5, pp. 585-595, May 2005.

Highnam, Dr. R.P., et al., "Mammographic image analysis", *Eur. J. Radiol.*, 24(1): 20-32, Jan. 1997.

Pisano, Etta D., et al., "Image Processing Algorithms for Digial Mammography: A Pictorial Essay", *Radiographics*, vol. 20, No. 5, pp. 1479-1491, Sep.-Oct. 2000.

Schaetzing, Ph.D., Ralph, et al., White Paper: "Agfa's MUSICA²™: Taking Image Processing to the Next Level", *AGFA Healthcare*, Apr. 24, 2007.

Smith, Ph.D., Andrew, White Paper: "Fundementals of Breast Tomosynthesis: Improving the Performance of Mammography", WP-00007 Jun. 2008.

May 6, 2010 International search report and written opinion in connection with International Application No. PCT/US2010/025937.

GE Healthcare, Essential for life: Senographe Essential Full-Field Digital Mammography System [online], 2006 [retrieved on Apr. 7, 2010]. Retrieved from the internet: <URL:http://www.gehealthcare.com/usen/xr/mammo/docs/SenoEssentialbrochure.pdf>.

* cited by examiner

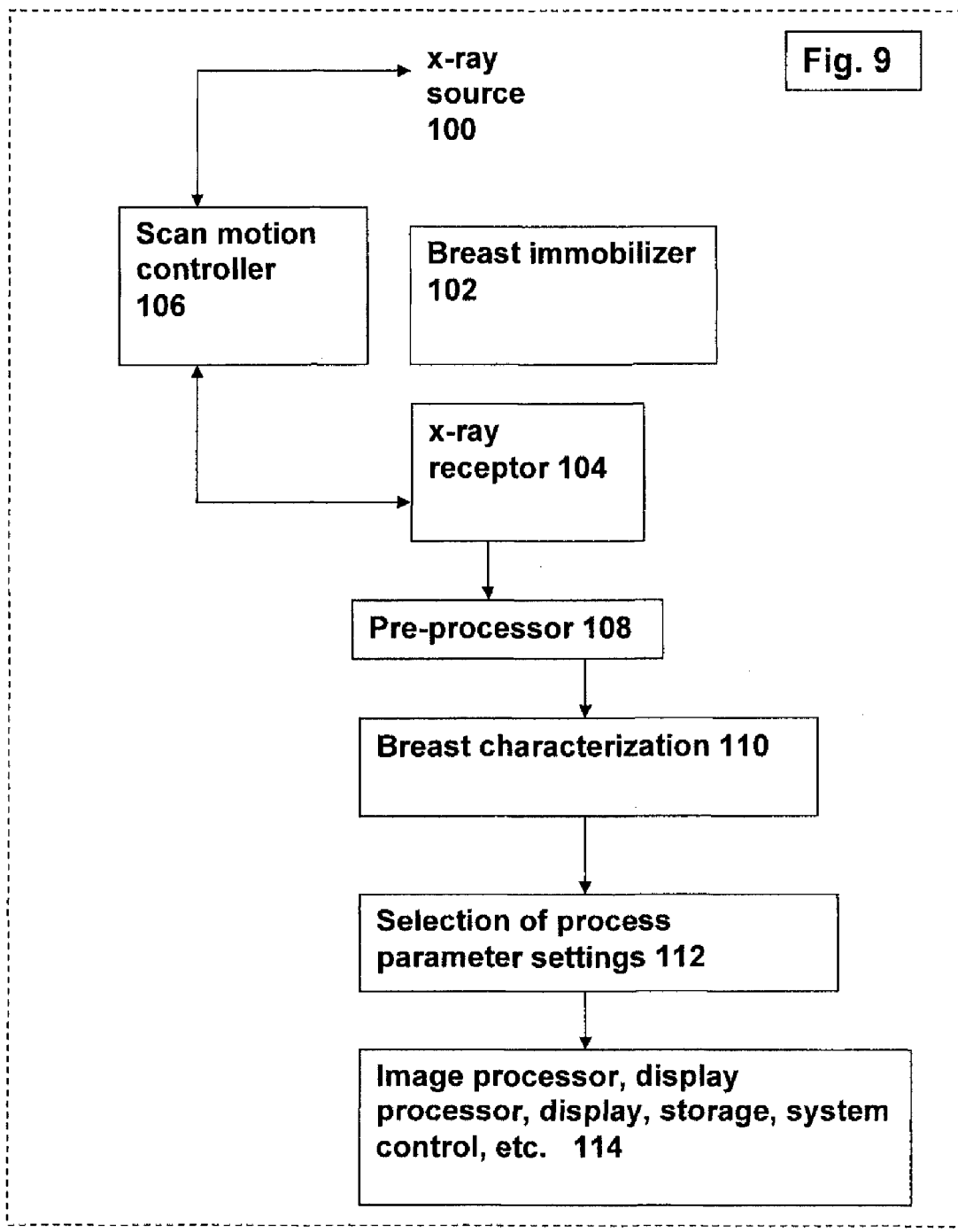

MAMMOGRAPHY/TOMOSYNTHESIS SYSTEMS AND METHODS AUTOMATICALLY DERIVING BREAST CHARACTERISTICS FROM BREAST X-RAY IMAGES AND AUTOMATICALLY ADJUSTING IMAGE PROCESSING PARAMETERS ACCORDINGLY

FIELD

This patent specification is in the field of medical x-ray imaging and more specifically relates to mammography and/or tomosynthesis methods and systems for imaging a patient's breast and yet more specifically relates to automatically deriving breast characteristics such as breast density and texture from breast x-ray images and automatically adjusting image processing parameters accordingly.

BACKGROUND

The breast images obtained directly from digital x-ray receptors typically are not suitable for screening or diagnosis and need to be computer-processed by algorithms that suppress image characteristics that are not believed to be helpful in identifying and assessing breast abnormalities and enhance image characteristics that are believed to be more useful. For example, such algorithms operate on the initial x-ray images from the x-ray receptor in digital mammography systems to reduce slowly varying density differences and high frequency noise, to enhance density difference likely to represent mid-size objects, to make the breast skin line more visible, and to smooth density variations near the skin line that are due to rapid changes in breast thickness. Typically, such image processing does not change between patients. It may differ somewhat between breast imaging systems, but tends to stay the same from image to image in the same system. An example of a mammography system in which such image processing is used is the Selenia™ digital mammography system available from the common assignee, Hologic, Inc. of Bedford, Mass. See brochure "Lorad Selenia™" Document B-BI-SEO US/Intl (May 6) copyright Hologic 2006. An example of a multi-mode system that can carry out conventional mammography as well as breast tomosynthesis in which such image processing is used is the Selenia Dimensions™ system, also available from the common assignee. See Smith, A., Fundamentals of Breast Tomosynthesis, White Paper, Hologic, Inc., WP-00007, June 08. Additional information regarding digital mammography, tomosynthesis and multi-mode systems offered by the common assignee can be found at <www.hologic.com>. See also, e.g., International Application WO 2006/058160 A2 published under the Patent Cooperation Treaty on Jun. 1, 2006 and Patent Application Publication No. US 2001/0038681 A1, PCT application International Publication No. WO 03/020114 A2 published Mar. 13, 2003, U.S. Pat. Nos. 7,142,633, 6,885,724, 6,647,092, 6,289,235, 5,051,904, 5,359,637, and 4,496,557, and published patent applications US 2004/0109529 A1, US 2004/0066884 A1, US 2005/0105679 A1, US 20050129172A1, and Digital Clinical Reports, Tomosynthesis, GE Brochure 98-5493, November 98. A tomosynthesis system specifically for imaging patients' breasts is disclosed in commonly owned U.S. Pat. Nos. 7,123,684 and 7,245,694. Systems and method for automatically deriving information of breast characteristics are discussed in published U.S. Patent Application US2007/0274585A1 and a breast CAD system is discussed in U.S. Pat. No. 5,657,362. A system manufacturer may offer processing the same initial image twice, for example, with two different image processing algorithms, where both resulting processed images are sent for review by a radiologist. See, for example, "Essentials for life, Senographe Essential Full-Filed Digital Mammography system," GE Healthcare brochure MM-0132-05.06-EN-US. The publications identified in this patent specification are hereby incorporated by reference herein.

SUMMARY

Breast composition can differ from one patient to another, from one breast to another of the same patient, and within a single breast. Such differences can manifest in breast characteristics such as x-ray density of the breast and texture of the breast. Some breasts are composed mainly of fatty tissue and are known as "fatty breasts," others have a high percentage of fibroglandular tissue and are known as dense breasts, and most are somewhere in the continuum between these two extremes. The most common purpose of breast imaging is to identify and assess potential pathologies or other abnormalities, which most frequently appear as likely microcalcifications, tumor masses, and architectural distortions. The advances described in this patent specification pertain to automatically identifying breast characteristics from information contained in the initial breast images, automatically selecting image processing algorithms and/or parameter settings for such algorithms, and using the algorithms and/or process parameter setting resulting from the selection to process the initial images into processed images from which display images can be obtained for presentation to health professionals or for other purposes such as further processing, e.g., CAD, distribution to work stations, sending to remote facilities, or storage in PACS facilities. The disclosed advances are applicable to conventional digital mammography systems as well as to tomosynthesis systems and multi-mode systems.

In one non-limiting example of the new approach, a breast x-ray imaging system using a digital x-ray image receptor acquires initial x-ray images of a patient's breast. Each initial image is represented by pixel values related to x-rays received at respective image pixels of the x-ray imaging receptor. The initial images typically but not necessarily are subjected to pre-processing such as gain correction and dark current correction. The system automatically derives from those images, breast characteristics related to selected properties of the imaged breast, such as, without limitation, breast x-ray density information and/or breast texture information. Based on the automatically derived information regarding breast properties, the system automatically selects process parameter settings of image processing algorithms that have adjustable process parameter settings. The system then processes the initial images using the image processing algorithms with the automatically selected adjustable settings to process the initial images into processed images and to obtain from them breast images suitable for display and/or other purposes.

In one example, the system classifies a breast in the continuum from fatty to dense, or as fitting in one of several ranges within that continuum, and then sets the image process parameters to settings appropriate to that breast. In another example, the system classifies individual regions within the breast and automatically selects process parameter settings appropriate to individual regions and appropriately adjusts the image processing algorithms for the respective breast regions so that the image processing varies locally within a breast image. In yet another example, the breast image parameters that are automatically derived include breast density texture in addition to or instead of breast x-ray density.

The image processing algorithms can include but are not limited to an unsharp mask filter, a multi-scale filter, and/or skin-line processing. The process parameter settings include, without limitation, weighting factors or effective filter kernel of the unsharp mask, different frequency bands or different frequency weights of the multi-scale filter, and enabling/disabling of individual ones of those algorithms.

BRIEF DESCRIPTION OF THE DRAWINGS

FIG. 9 is a block diagram of a system implementing breast processing automatically adjusted based on automatically derived breast characteristics.

DETAILED DESCRIPTION OF PREFERRED EMBODIMENTS

In describing preferred embodiments, specific terminology is employed for the sake of clarity. However, this patent specification is not intended to be limited to the specific terminology so selected and it is to be understood that each specific element includes all technical equivalents that operate in a similar manner. In addition, a detailed description of known functions and configurations will be omitted when it may obscure the subject matter of the invention described in the appended claims.

Figure 1:
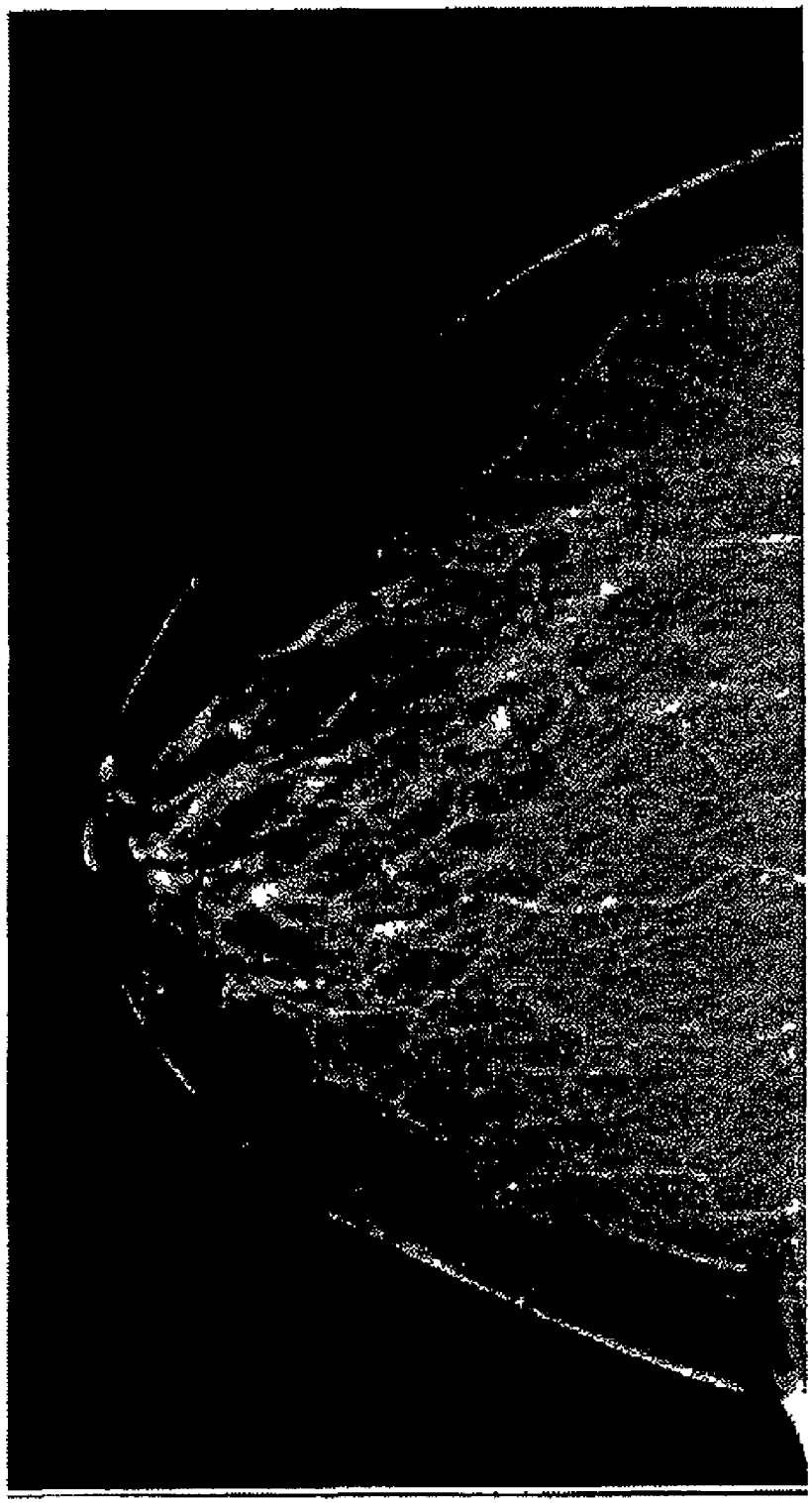
FIG. 1 is a mammogram illustrating a fatty breast.
Figure 2:
FIG. 2 is a mammogram illustrating a mid-density breast.
Figure 3:
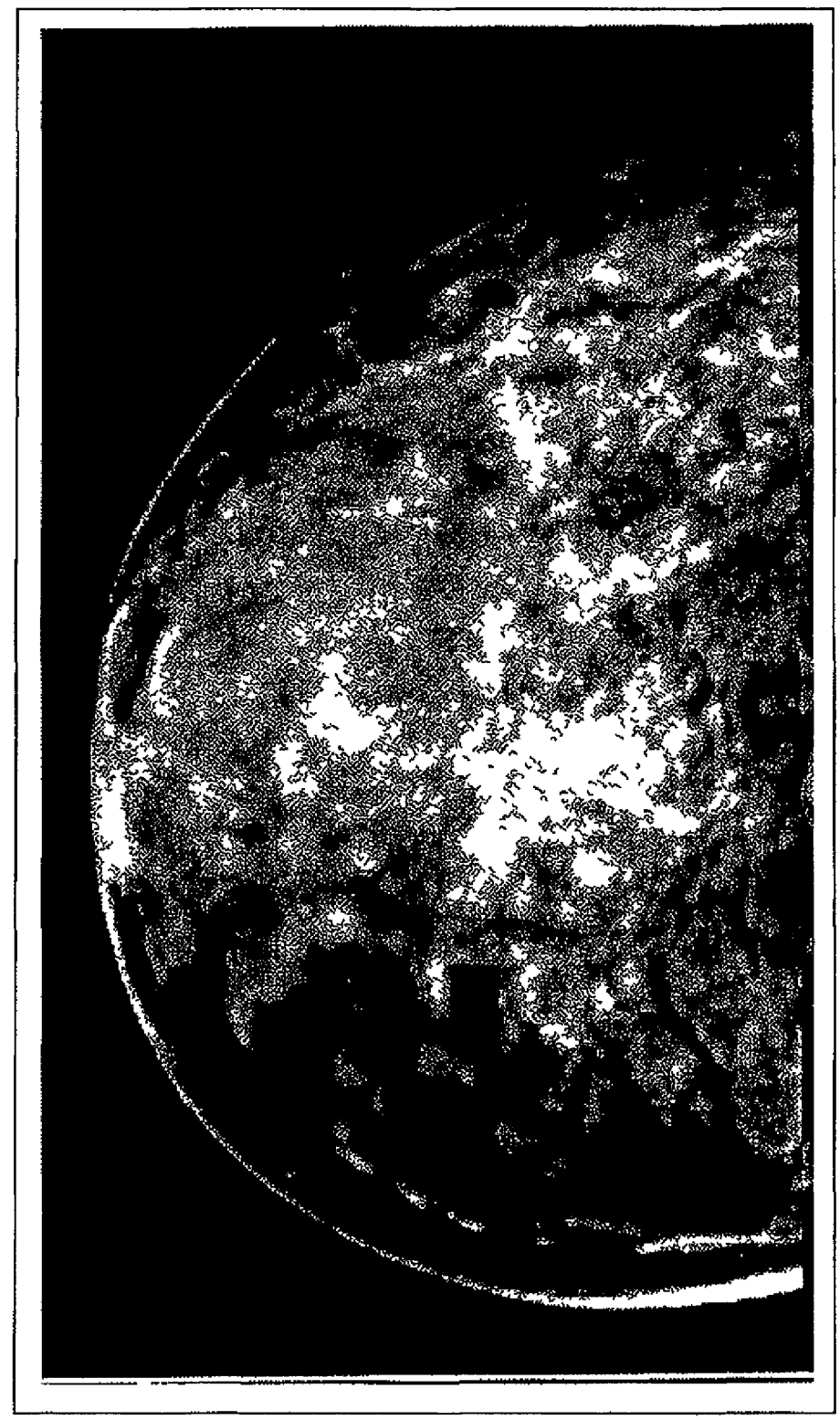
FIG. 3 is a mammogram illustrating a dense breast.

FIGS. 1-3 are mammograms of breasts having different x-ray densities. FIG. 1 is an example of a fatty breast, FIG. 2 is an example of a mid-density breast, and FIG. 3 is an example of a dense breast. According to preferred examples of the new approach described in this patent specification, different image processing algorithms are applied to images of the breasts seen in the mammograms of FIGS. 1-3, as discussed in more detail below.

Figure 4:
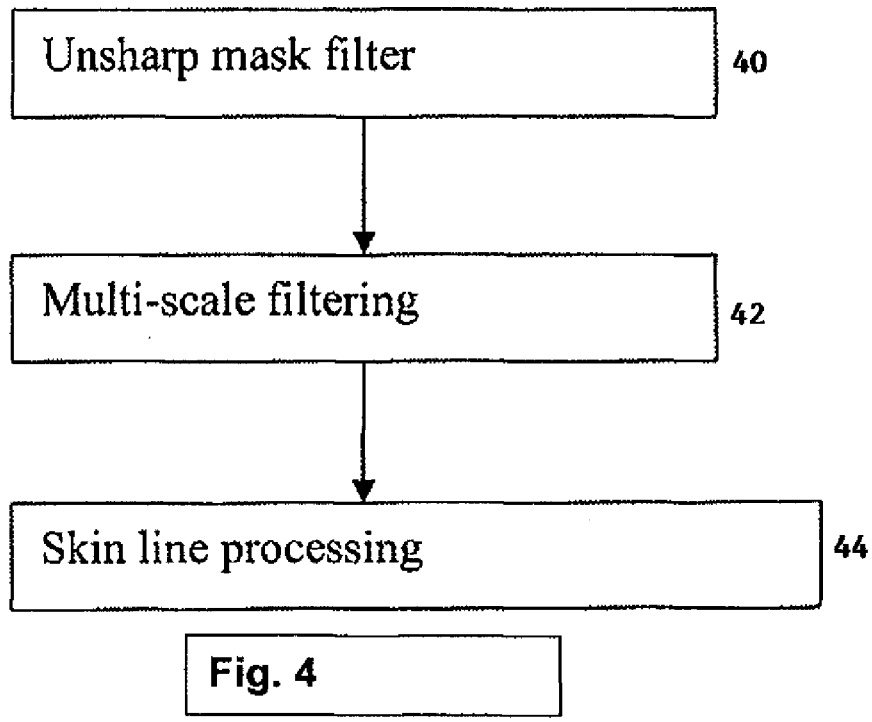
FIG. 4 is a flow chart illustrating image processing algorithms applied to initial x-ray images of a patient's breast.

FIG. 4 illustrates examples of image processing algorithms applied to initial breast images obtained from a digital x-ray receptor of a mammography system such as the Selenia™ digital mammography system identified above. An initial breast image from the digital x-ray receptor, which initial image may have already undergone pre-processing such as gain calibration and/or other known pre-processing, is subjected to an unsharp mask filter in step 40, the resulting filtered image is subjected to multi-scale filtering at step 42, and the filtered image resulting from step 42 is supplied to skin-line processing in step 44. The output of processing step 44 is a processed breast image from which a display image can be obtained through known further processing. If the processed image from step 44 is a mammogram, such further processing can include CAD (computer aided detection) to identify suspected abnormalities, for example using mammography CAD products available from R2 Technology, Inc. of Santa Clara, Calif., preparing the image for display, transferring the image to a workstation, and including the image in a display protocol sequence. If the processed image from step 44 is a projection tomosynthesis image, the further processing can include, in addition to some of the processing applicable to mammograms, reconstructing a slice image from several projection images using known tomosynthesis slice image reconstruction algorithms. Each of the algorithms of steps 40, 42 and 44 includes process parameter settings that can be selected for processing any one breast image. For example, the optimal set of process parameter settings for a fatty breast in general is not the same as the optimal set of process parameter settings for a dense breast. For example, strong background suppression may be more appropriate for a dense breast image, in order to allow the visibility of objects lying in a changing background, but in an image of a fatty breast, where the background is more slowly varying, strong background suppression may result in the generation of too much contrast where no anomaly of interest is present. Thus, for a dense breast the unsharp mask filter may be adjusted to suppress the background to a greater degree than for a fatty breast. See, for example, (1) RadioGraphics 2000; 20:1479-1491, Pisano E T, et al., Image Processing Algorithms for Digital Mammography: A Pictorial Essay; (2) White Paper, Schaetzing R., Agfa MUSICA™, Taking Image Processing to the Next Level, AGFA Healthcare, Update 24 Apr. 2007; and (3) Cole E., et al., The Effects of Gray Scale Image Processing on Digital Mammography Interpretation Performance, Academic Radiology, Volume 12, Issue 5, pages 585-595.

Figure 5:
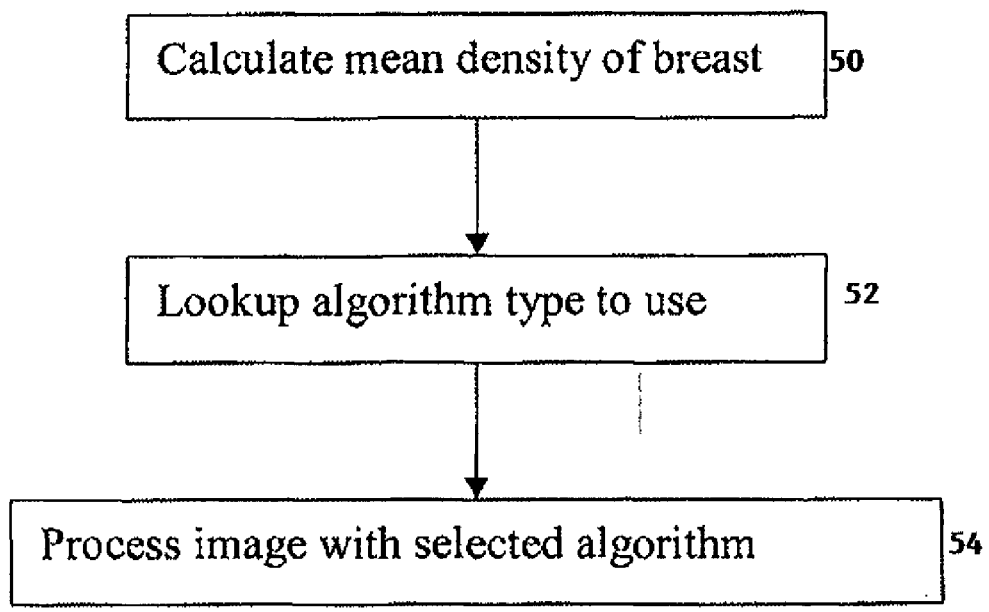
FIG. 5 is a flow chart illustrating automated calculation of mean density of a breast image and using the result to automatically select process parameter settings for image processing algorithms applied to the initial breast image.

FIG. 5 illustrates an example of automatically deriving breast characteristics related to selected properties of the imaged breast, using for the purpose information from the initial breast images. At step 50 the system calculates or estimates an overall density of the breast, for example by finding the mean density of the breast from the pixel values in the breast image. This can be done through a process that finds the arithmetic mean of the pixel values in an image by adding all pixel values and dividing the result by the number of pixel values. At step 52, the system uses information from the mean, such as the value of the mean, to address a lookup table that contains process parameter settings for processes such as those in FIG. 4. The process parameter settings can include an enable/disable parameter for each of the processes of FIG. 4. The process parameters settings of the unsharp mask filter of step 40 can include parameters settings such as different weights for the unharp mask suppression, different effective filter kernels, and/or different shapes of the filter pattern. The parameters settings of the multi-scale filter can include different frequency weights that characterize the filter and/or how each different frequency band if the filter is emphasized or attenuated. Other types of filters can be used instead of multi-scale filtering. A general frequency domain filter, where the amplitudes at each spatial frequency characterize the strength of the filtering can be used to generate an filtering operation comparable to multi-scale filtering. The lookup table can be a table that has a row for each mean density in the likely range of mean densities that can come from step 50, with each row containing process parameter setting for each of the processes to be applied to the image in the process of FIG. 4. More typically, each row of the table pertains to a range of mean densities rather than a single mean density value. For example, the lookup table can be derived empirically, by testing in which a process such as one of the processes of FIG. 4 is applied to an image of a breast or a phantom with a particular mean density to determine which settings for that process give the best result, and those settings are stored for that process and for that mean density in the lookup table. The process is repeated for different mean densities and different process parameter settings for each different image processing algorithms to complete the lookup table. Typically, the lookup table contains process parameter values for mean density values in steps of more than one unit of mean density so that the settings in a row are used for a range of mean densities or settings are interpolated from the nearest rows when the measured mean density of a breast is different from the densities in the table. For example, for processing the image of a fatty breast: (1) the unsharp mask is enables to operate in accordance with $x'=x+k*(x-<x>)$, where $x=x(l,j)$ is the input value of a pixel at position $(i,j)$ in the image to be processed by the unsharp filter, $<x>$ is the smoothed pixel value in the neighborhood of pixel position $(l,j)$, k is the weight of the unsharp mask, and $x'$ is the new pixel value resulting from the application of the unsharp mask; and (2) the Fourier filter kernel has an amplitude that essentially does not change with spatial frequency. In the same example, for processing the image of a dense breast: (1) the unsharp mask is disabled so that $k=0$ and the expression becomes $x'=x+0*(x-<x>)$; and (2) the Fourier filter kernel has an amplitude that initially gradually increases with spatial frequency and then rapidly drops in amplitude with further increase of spatial frequency within the range of spatial frequencies relevant to the breast image.

Other ways of deriving breast characteristics from initial breast images can be used in addition to or instead of those described above. For example, ways of classifying breast images are discussed in Highnam R P, Brady J M, Shepstone B J, Mammographic image analysis, Eur J Radiol. 1997 January; 24(1):20-32. The article is hereby incorporated by reference in this patent specification. Still other ways are discussed in said published U.S. Patent Application US 2007/0274585 A1 (see, e.g., paragraphs 73 and 74) and U.S. Pat. No. 5,657,362 (see, e.g., FIG. 7).

In step 54, the system processes the initial image through the steps of FIG. 4, using the process setting obtained from the lookup table by addressing it with the mean density derived in step 50. The addressing can be directly with the mean density value, or indirectly, with an address derived from the mean density value. The address can point to a specific row in the lookup table, in which the process parameter settings of that row are used in step 54, or the address can point between two rows in the lookup table, in which case step 54 can se process parameter settings interpolated from the two or more nearest rows in the lookup table. If desired, the interpolation can use weighting factors that provide greater contribution from rows closer in density to the measured breast density used in addressing the table.

In can be desirable to have uniform process parameters to all of the initial breast images in a particular set of images, for example to the two CC views and the two MLO views of a patient's breasts taken in a single x-ray examination, or only the views of one of the breasts, or only the same views of each breast, so as to reduce differences in image appearance between the display images of a set. In this case, the process parameter settings can be selected based on some selected composite breast characteristics of the set of images to which the same process parameter settings are to be applied.

Figure 6:
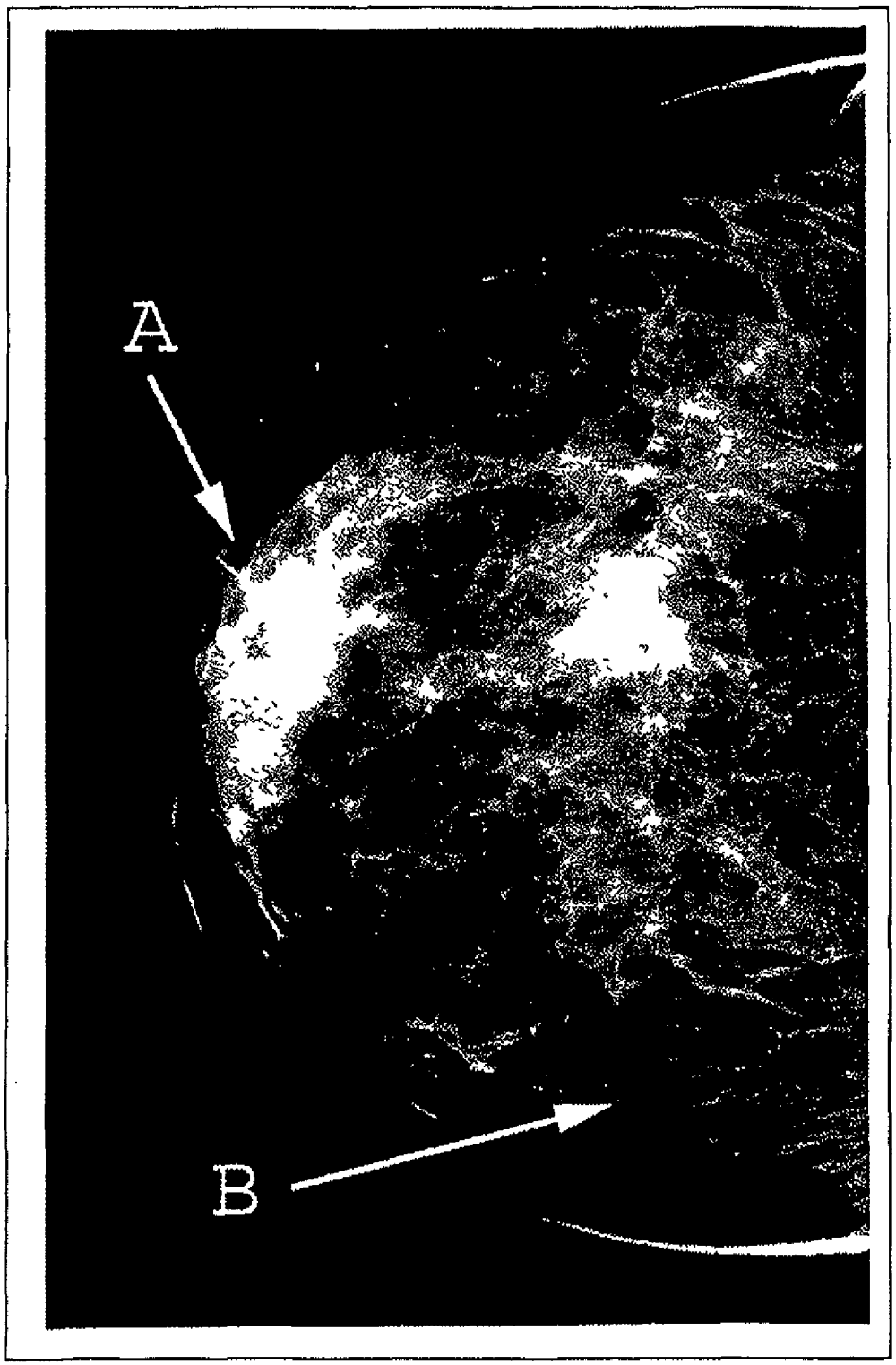
FIG. 6 illustrates a breast image in which a fatty region is processed with one set of image process parameter settings while a dense region is processed with a different set of image processing parameter settings.

In addition to differences in breast characteristics between different patients or the left and right breasts of the same patient, or the MLO vs. the CC views of a patient, there can be pertinent differences between regions of a breast. In accordance with another non-limiting example, the system and process described in this patent specification can take such differences into account to improve the processing the initial breast images. Specifically, different regions within the breast can be processed using different process parameter settings. FIG. 6 shows an example of a mammogram processed by using different parameter settings for different regions. Region A is a dense region of the breast and is processed using different process parameter settings from fatty region B.

Figure 7:
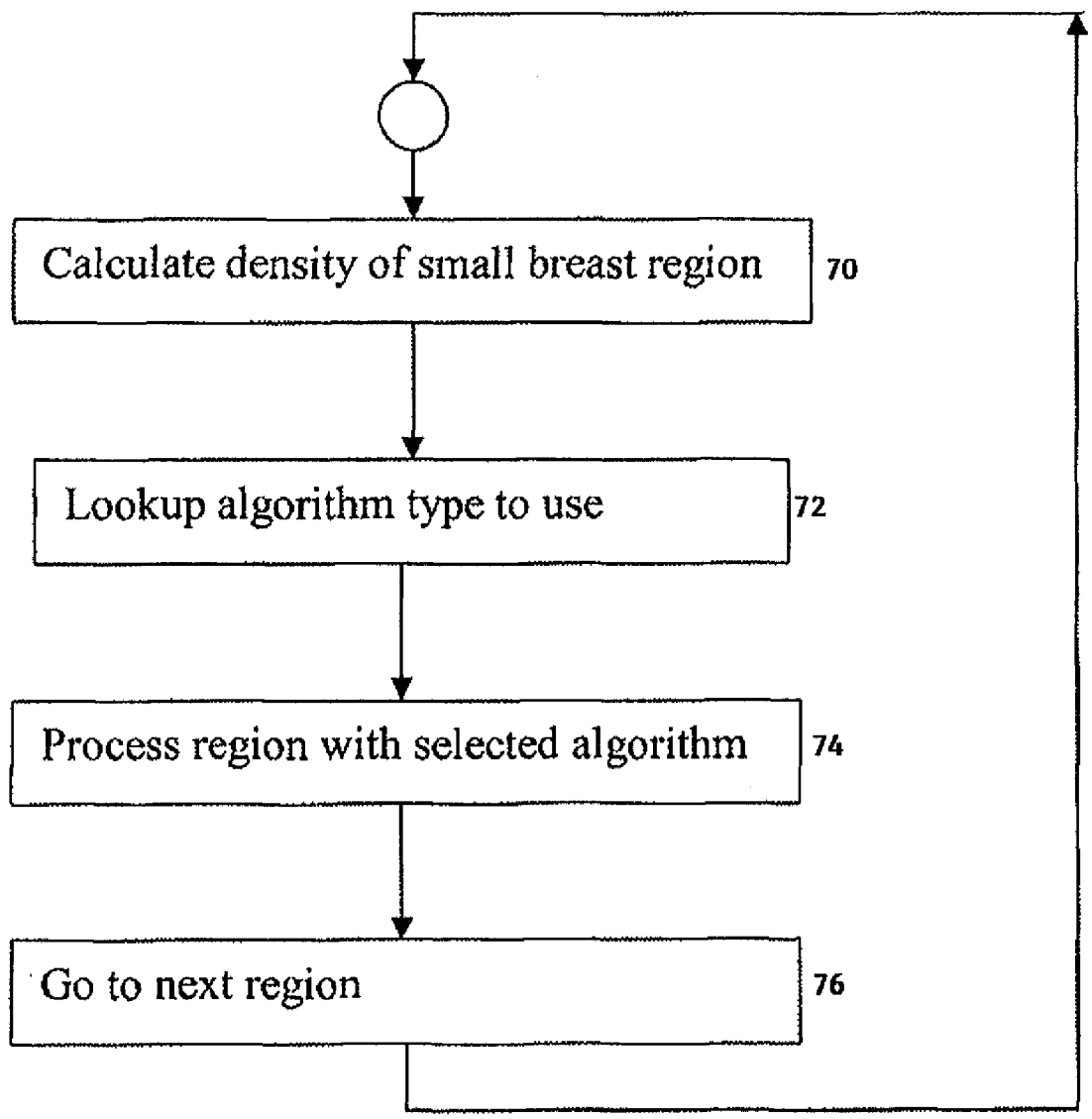
FIG. 7 is a flow chart illustrating processing different regions of a breast image with different sets of image process parameter settings.

FIG. 7 illustrates different processing for different internal regions of the breast image. Step 70 receives a portion of an initial breast image that has been segmented based on average density, for example. Specifically, an initial breast image is segmented through a process that assigns respective x-ray density values to relatively small regions of the image. As a simplified and non-limiting example, the segmentation process can divide the image into an array of relatively small contiguous regions, e.g. rectangular regions except for regions adjacent the skin line, and calculate or estimate the mean density of each respective region. As another non-limiting example, a segmentation process can identify regions of irregular shape in which the pixel density values are above a specified value, below a specified value, and/or within specified ranges of pixel values. The mean pixel values of a first such region are calculated or estimated in step 70 and the resulting density value or an address derived therefrom is used in step 72 to address a lookup table to thereby select process parameter settings that are used in step 74 to process the first region with algorithms using these process parameters. Step 76 selects the next region, and the process returns to step 70 to calculate or estimate a density value, and continues through step 76 until all regions have been processed. The resulting processed regions of the initial image then are integrated into a processed breast image and used for further processing for display or other purposes. Such integration can involve a process for sufficiently smoothing the edges of the regions that are being assembled into a processed breast image to avoid undesirable appearance of seams. Such smoothing can use known image blending algorithms used to blend an insert from one image into another image.

Figure 8:
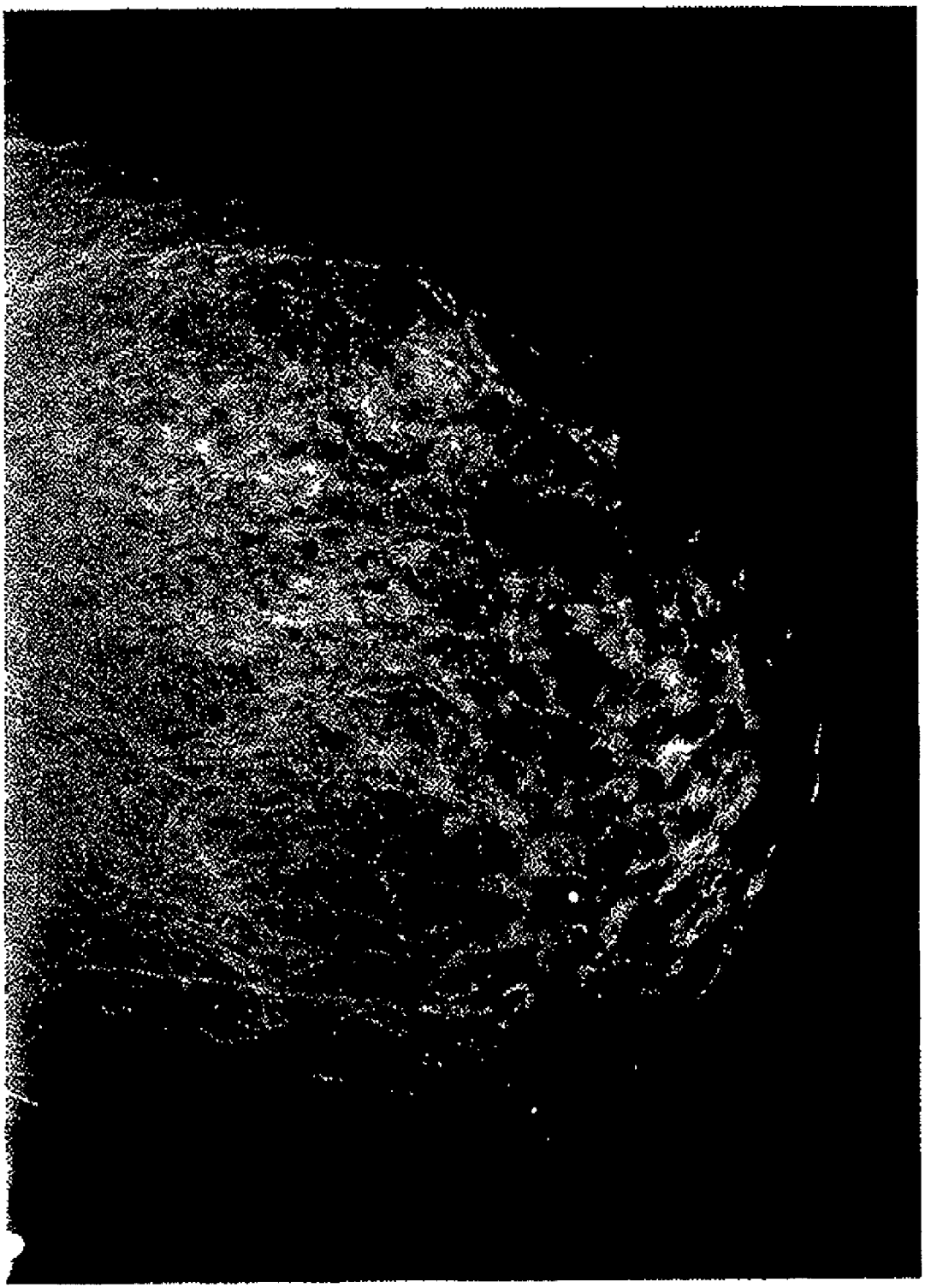
FIG. 8 is a mammogram illustrating a breast exhibiting high frequency texture.

While global and local mean densities are the characteristics used in the above-described examples, other breast characteristics can be used in addition to or instead of mean density to select appropriate process parameter settings. One example of such other characteristics is breast texture, and FIG. 8 illustrates a mammogram exhibiting high frequency texture. A process of classifying breast texture can make use of the spatial frequency and gradients of changes in pixel values when scanning the pixels of an initial image. The resulting quantitative characterization of the entire breast, or of regions in the breast, can be used to derive address information and to address a lookup table that can be empirically populated with process parameter settings in a manner similar to the lookup table discussed above that is addressed based on global or local density values. The term "global" refers to a characteristic that is the same for an entire breast image or for a set of breast images. The texture information and density information can be combined into a single address, or only one or the other can be use to address a lookup table of process parameter settings, or each can be used to address a separate table. A set of image processing algorithms with settings from a table addressed with density information can be applied to an initial image or region thereof, and another set of image processing algorithms can be applied to the resulting processed image with settings from a table addressed with breast texture information, or the order of the two sets of algorithms can be reversed or otherwise changed.

FIG. 9 illustrates a system in which various examples of the processes described above can be implemented. The system comprises an image acquisition unit that includes an x-ray source 100 on one side of a breast immobilizer 102 and an x-ray receptor 104 on the other side. For mammography, source 100, immobilizer 102 and receptor 104 remain in a fixed rotational relationship and move together under the control of controller 106 from one imaging position to another, e.g., from a CC position to an MLO position. For tomosynthesis data acquisition, scan motion controller 106 moves source 100 relative to immobilizer 102. Receptor 104 also moves relative to immobilizer 102 during tomosynthesis data acquisition in said Selenia Dimensions™ system but may move differently, or not at all, in other systems. Typically, the motion is motorized. The source motion can be continuous or the source can stop and emit imaging x-rays at one projection angle before moving to another projection angle. X-ray receptor 104 provides projection image data in the form of an array of pixel values related to incident x-ray energy. The pixel values representing the initial images from x-ray receptor 104 typically are not suitable for display in their raw form. They can be subjected to pre-processing in unit 108, such as conventional pre-processing for gain correction, dark current correction, and other known pre-processing. The pre-processed initial images, or the raw initial images from receptor 104, are supplied to breast characterization unit 110 for automatically deriving breast characteristics, for example as discussed in connection with FIG. 5. The breast characteristics derived in unit 110 are used to automatically select appropriate process parameter settings in unit 112, the initial images together with the appropriate process parameter settings are supplied to unit 114 for processing as described in connection with FIG. 4, for example, and the resulting processed breast images are further processed for display or other purposes, and are used accordingly. Pre-processor 108 and units 110, 112 and 114 can be implemented by programming a computer that already is included in a system such as the Selenia™ and the Selenial Dimensions™ systems or a workstation such as available from the common assignee, such computer or workstation being programmed to carry out one or more examples of the processes disclosed above.

The foregoing description of preferred embodiments has been presented as an illustration of examples and is not intended to be exhaustive or to limit the claimed inventions to the specific examples. Those examples are intended to describe principles that persons skilled in the art may use to practice the claimed inventions, using variations and modifications of the disclosed examples that are suited to a particular environment. It is intended that the scope of the invention be defined by the appended claims and their equivalents.

The invention claimed is:

1. A breast x-ray imaging method comprising:
   acquiring one or more initial x-ray images of a patient's breast, each of said images being represented by pixel values related to x-rays received at respective image pixel positions of an x-ray imaging receptor;
   automatically deriving, from said one or more initial x-ray images of the breast, breast characteristics related to selected properties of the imaged breast;
   automatically selecting, based at least in part on the derived breast characteristics, process parameter settings of image processing algorithms having adjustable process parameter settings;
   processing said one or more initial breast images with said image processing algorithms using the selected process parameter settings to thereby derive one or more processed breast images;
   obtaining one or more display images of the breast from said one or more processed breast images; and
   selectively displaying the one or more display images for screening or diagnosis on one or more display devices.

2. A breast x-ray imaging method as in claim 1 in which the deriving step comprises deriving respective breast characteristics for different internal regions of the breast, the selecting step comprises deriving respective different process parameter settings for said internal regions, and the processing step comprises processing said internal regions of the initial breast images using the respective different process parameter settings.

3. A breast x-ray imaging method as in claim 1 in which said processing comprises applying to the initial breast images one or more of an unsharp mask filter, a multi-scale filter, and skin-line processing.

4. A breast x-ray imaging method as in claim 1 in which said process parameter settings are selected from the group consisting of weighting factors or effective filter kernel of an unsharp mask filter, and different frequency bands or different frequency weights of a multi-scale filter.

5. A breast x-ray imaging method as in claim 1 in which said breast characteristics comprise at least one of x-ray breast density and breast texture.

6. A breast x-ray imaging method as in claim 1 in which said breast characteristics comprise a mean x-ray density of the imaged breast.

7. A breast x-ray imaging method as in claim 1 in which a single set of said breast characteristics is derived from a set of several breast images of the same patient in said deriving step, said single set of breast characteristics is used to select a single set of process parameter settings in said selecting step, and the single set of process parameter settings is used in the processing step to process each of the initial images in the set.

8. A breast x-ray imaging method as in claim 1 in which the acquiring step comprises exposing the patient's breast to imaging x-rays in a mammography system.

9. A breast x-ray imaging method as in claim 1 in which the acquiring step comprises exposing the patient's breast to imaging x-rays in a breast tomosynthesis system and said initial images comprise a set of projection images of the patient's breast taken at different angles of the imaging x-rays to the patient's breast.

10. A breast x-ray imaging system comprising:
   an acquisition station including an x-ray source, an x-ray imaging receptor, and a breast platform between the source and the receptor, said receptor acquiring one or more initial x-ray images of a patient's breast positioned on said platform and irradiated with x-rays from said source;
   a processor receiving said initial images and configured to automatically derive therefrom breast characteristics related to selected properties of the imaged breast;
   said processor being further configured to automatically select, based at least in part on the derived breast characteristics, process parameter settings of image processing algorithms having adjustable process parameter settings;
   said processor being still further configured to process said one or more initial breast images with said image processing algorithms using the selected process parameter settings to thereby derive one or more processed breast images; and
   a display processor configures to receive said processed breast images, obtain one or more display images of the breast therefrom, and selectively display said display images of the breast for screening or diagnosis.

11. A breast x-ray imaging method as in claim 10 in which said breast characteristics comprise a mean x-ray density of the imaged breast.

12. A breast x-ray imaging system as in claim 10 in which the processor is configured to derive respective breast characteristics for different internal regions of the initial breast images and select respective different process parameter settings for said internal regions and process said internal regions of the initial breast images using the respective different process parameter settings.

13. A breast x-ray imaging system as in claim 10 in which said processor is configured to apply to said initial images algorithms that comprise one or more of an unsharp mask filter, a multi-scale filter, and skin-line processing.

14. A breast x-ray imaging system as in claim 10 in which said process parameter settings selected by said processor comprise at least some of weighting factors or effective filter kernel of an unsharp mask filter, and different frequency bands or different frequency weights of a multi-scale filter.

15. A breast x-ray imaging method as in claim 10 in which said breast characteristics comprise texture of the imaged breast.

16. A computer program product embodied in a non-transitory form in a physical computer program medium, said computer program product when running in a computer coupled with an x-ray imaging system that supplies the computer with initial x-ray images of a patient's breast, causing the computer to:

automatically derive, form said initial x-ray images of the breast, breast characteristics related to selected properties of the imaged breast;

automatically select, based at least in part on the derived breast characteristics, process parameter settings of image processing algorithms having adjustable process parameter settings;

process said one or more initial breast images with said image processing algorithms using the selected process parameter settings to thereby derive one or more processed breast images;

obtain one or more display images of the breast from said one or more processed breast images; and selectively cause a display device to displaying the one or more display images for screening or diagnosis.

17. A computer program product as in claim 16, causing the computer to derive respective breast characteristics for different internal regions of at least one initial breast image and select respective different process parameter settings for said internal regions and process said internal regions using the respective different process parameter settings.

18. A computer program product as in claim 16, causing the computer to apply to said initial images algorithms that comprise one or more of an unsharp mask filter, a multi-scale filter, and skin-line processing.

19. A computer program product as in claim 16, in which said process parameter settings comprise at least some of weighting factors or effective filter kernel of an unsharp mask filter, and different frequency bands or different frequency weights of a multi-scale filter.

20. A computer program product as in claim 16, in which said breast characteristics comprise at least one of mean x-ray density and texture of the imaged breast.

\* \* \* \* \*